US00PP25792P2

(12) United States Plant Patent
Luby

(10) Patent No.: US PP25,792 P2
(45) Date of Patent: Aug. 11, 2015

(54) BLUEBERRY PLANT NAMED 'MNPINK1'

(50) Latin Name: ***Vaccinium* hybrid**
Varietal Denomination: MNPink1

(71) Applicant: James Luby, St. Paul, MN (US)

(72) Inventor: James Luby, St. Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 94 days.

(21) Appl. No.: 13/998,872

(22) Filed: Dec. 17, 2013

Related U.S. Application Data

(60) Provisional application No. 61/848,592, filed on Jan. 7, 2013.

(51) Int. Cl.
*A01H 5/00* (2006.01)

(52) U.S. Cl.
USPC ..... Plt./157

(58) Field of Classification Search
USPC ..... Plt./157
See application file for complete search history.

*Primary Examiner* — Annette Para
(74) *Attorney, Agent, or Firm* — Penny J. Aguirre

(57) ABSTRACT

A new cultivar of *Vaccinium*, 'MNPink1', characterized by its pink berries, its moderately crisp berries that have a blueberry taste with desirable aroma and sugar-acid balance, its maroon fall foliage color, its mid size plant stature; reaching about 1.25 m in height and 1.4 m in width as a mature (25-year-old) plant, and its reliably cold hardiness and productivity in U.S.D.A. Zone 4.

3 Drawing Sheets

Botanical classification: *Vaccinium* hybrid.
Cultivar designation: 'MNPink1'.

BACKGROUND OF THE INVENTION

The present invention relates to a new and distinct cultivar of *Vaccinium* spp. named 'MNPink1' and is hereinafter referred to by the cultivar name 'MNPink1'. 'MNPink1' represents a new cultivar of half-high blueberry (derived from the species *V. corymbosum* and *V. angustifolium*) that is grown primarily as a home garden and landscape plant.

The new cultivar was discovered as a seedling by the Inventor in Becker, Minn. The Inventor sowed seeds that were pooled from crosses made between unnamed proprietary plants in his breeding program in 1983. The Inventor selected 'MNPink1' in 1987 as a single unique plant amongst the seedlings that resulted from the above crosses. The exact parentage is unknown.

Asexual propagation of the new cultivar was first accomplished by the Inventor by semi-hardwood cuttings in Becker, Minn. in 1988. Asexual propagation of the new cultivar by semi-hardwood cuttings has shown that the unique features are stable and reproduced true to type in successive generations.

SUMMARY OF THE INVENTION

The following traits have been repeatedly observed and represent the characteristics of the new cultivar. These attributes in combination distinguish 'MNPink1' as a new and unique cultivar of *Vaccinium*.

1. 'MNPink1' exhibits pink berries as described herein.
2. 'MNPink1' exhibits moderately crisp berries that have a blueberry taste with desirable aroma and sugar-acid balance.
3. 'MNPink1' exhibits maroon fall foliage color.

4. 'MNPink1' exhibits a slightly upright and bushy plant habit.
5. 'MNPink1' exhibits a mid size plant stature; reaching about 1.25 m in height and 1.4 m in width as a mature (25 year-old) plant in central Minnesota.
6. 'MNPink1' has been shown to be reliably cold hardy and productive in U.S.D.A. Zone 4.

'MNPink1' can be most closely compared to the cultivars 'Pink Lemonade' (not patented) and 'Pink Champagne' (not patented), and 'Northblue' (not patented). 'Pink Lemonade' and 'Pink Champagne' are similar to 'MNPink1' in having berries that are pink in color, but both differ from 'MNPink1' most significantly in having darker pink berries and in having irregular or poor fruit crops when grown in northern climates due to having southern blueberry species in their breeding history. 'Pink Lemonade' is a hexaploid blueberry whereas 'Pink Champagne' and 'MNPink1' are tetraploid blueberries. 'Northblue' is similar to 'MNPink1' in being a half high blueberry cultivar with good fruit production in northern climates (U.S.D.A. Zone 4). 'Northblue' differs from 'MNPink1' in having blue fruit, in having a more dwarf plant habit that is less upright with more branching.

BRIEF DESCRIPTION OF THE DRAWING

The accompanying colored photographs illustrate the overall appearance and distinct characteristics of the new *Vaccinium* cultivar. The photographs were taken of five year-old plants of the new cultivar as grown outdoors in a field in Becker, Minn.

The photograph in FIG. 1 provides a view of a fruit-bearing plant of 'MNPink1' in fruit.

Figure 1:
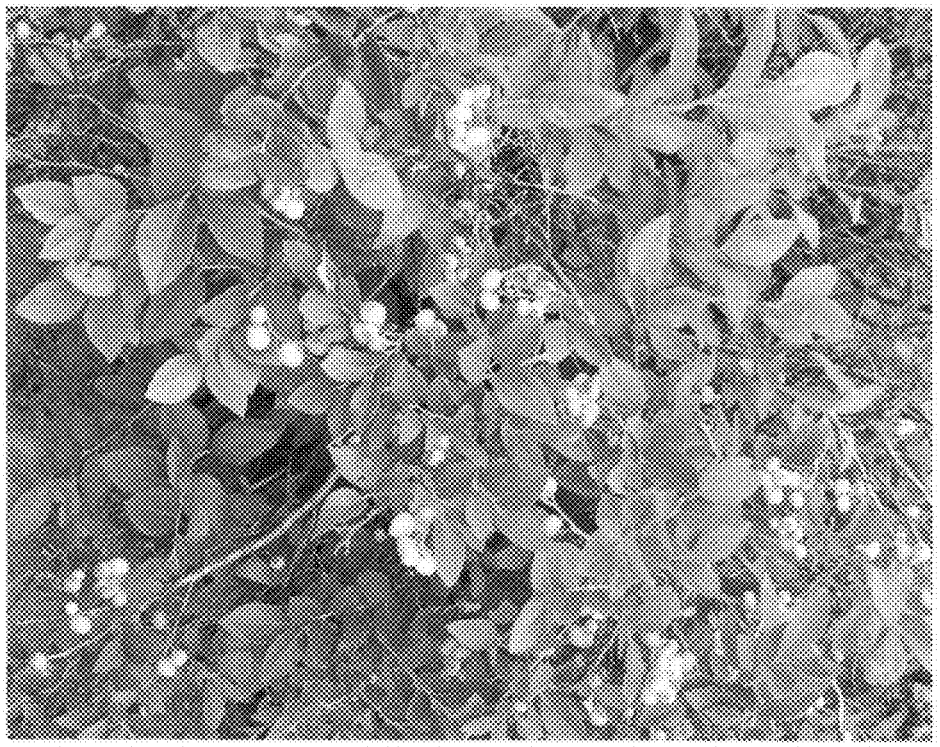
Figure 2:
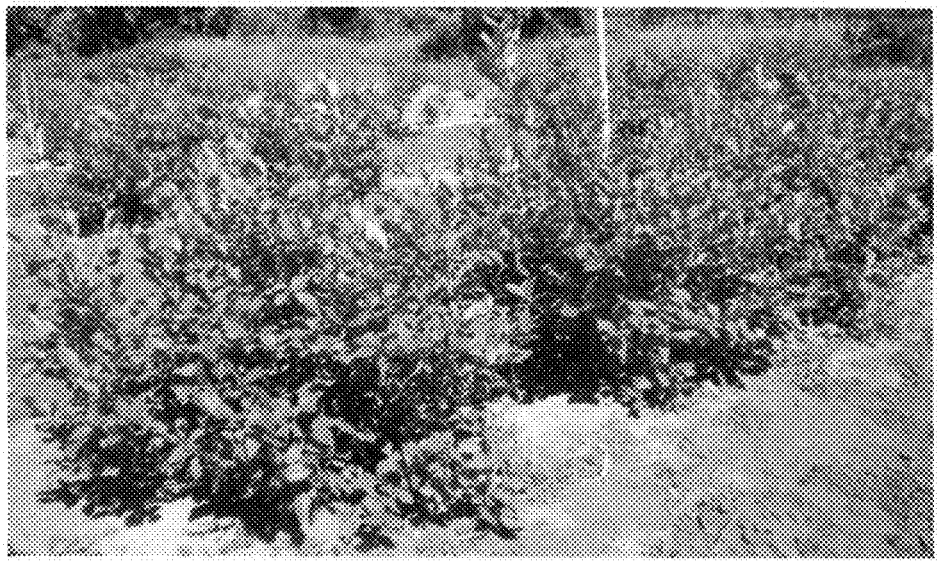

The photograph in FIG. 2 provides a view of the plant habit of 'MNPink1'.

Figure 3:
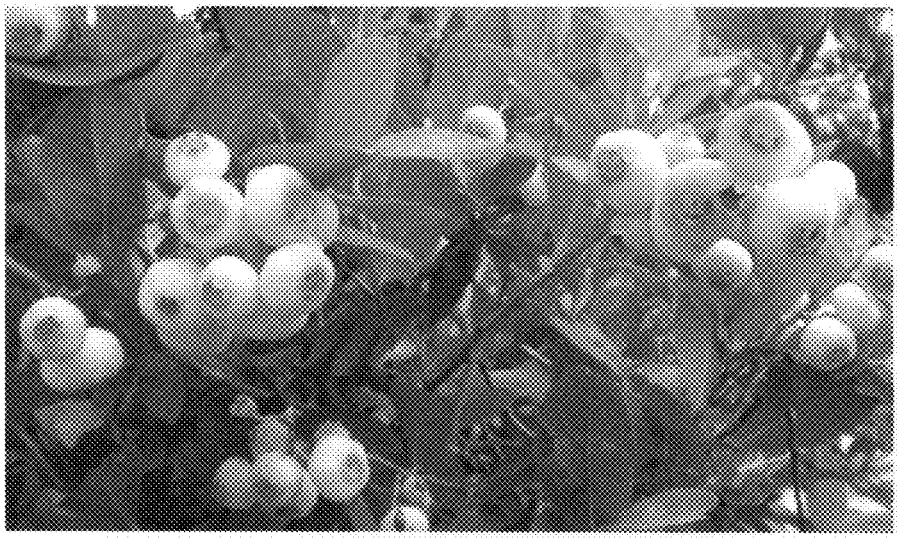

The photograph in FIG. 3 provides a close-up view of ripe and nearly ripe fruit on a plant of 'MNPink1'.

Figure 4:
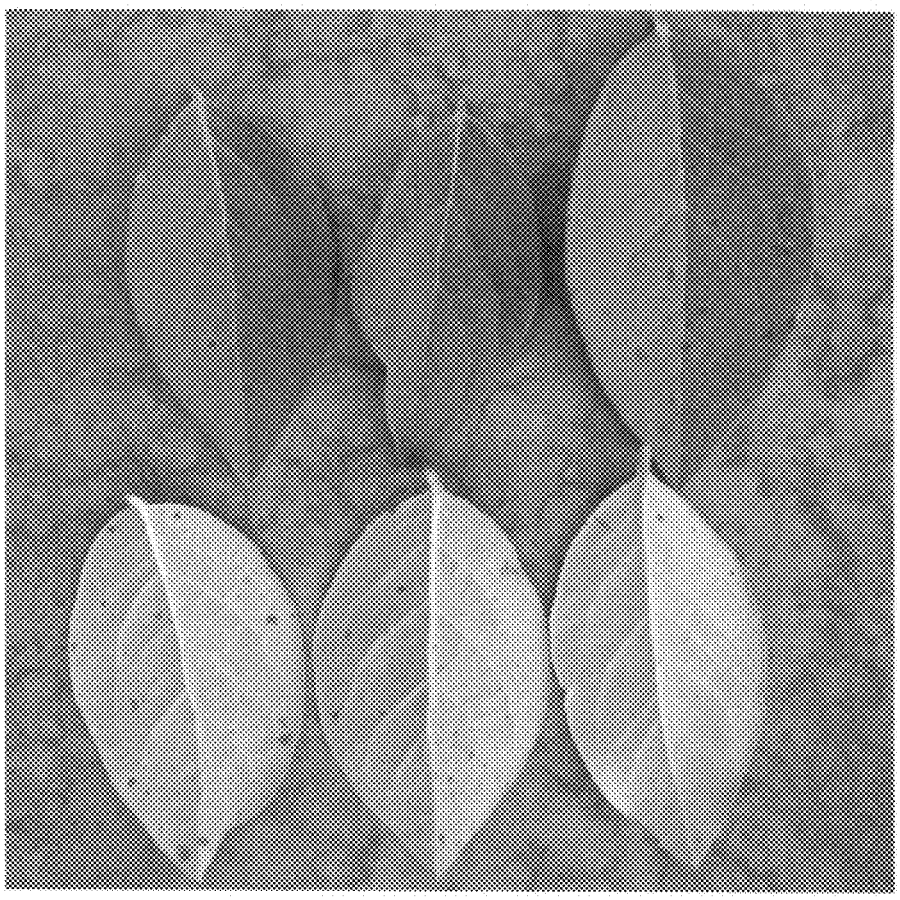

The photograph in FIG. 4 provides a close-up view of the upper surface (top) and lower surface (bottom) of mature, fully expanded leaves of 'MNPink1' at the time of fruit ripening.

Figure 5:
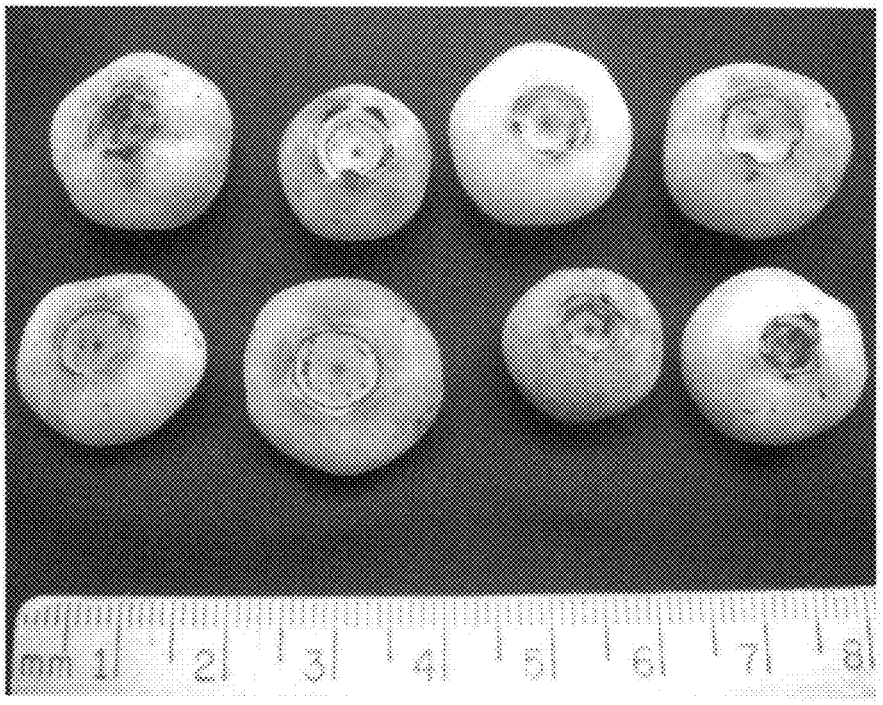

The photograph in FIG. 5 provides a close-up view of the calyx end of ripe fruit of 'MNPink1'.

Figure 6:
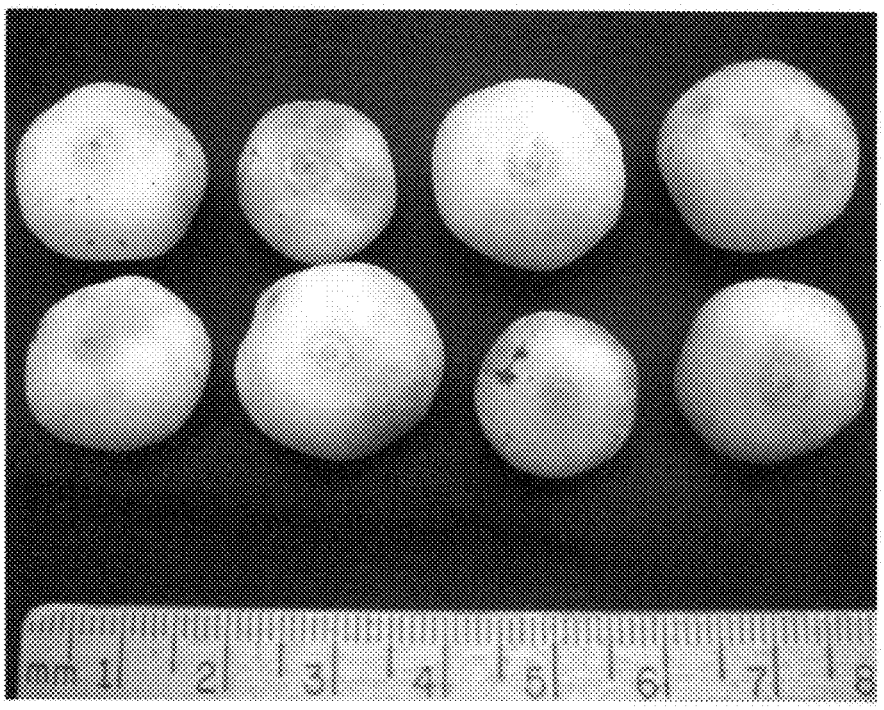

The photograph in FIG. 6 provides a close-up view of the pedicel end of ripe fruit of 'MNPink1'.

The colors in the photographs are as close as possible with digital photography techniques available, the color values cited in the detailed botanical description accurately describe the colors of the new cultivar of *Vaccinium*.

DETAILED BOTANICAL DESCRIPTION OF THE PLANT

The following is a detailed description of plants 5 years in age (except where noted otherwise) as grown outdoors in a trial field in Becker, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Deciduous shrub.

*Plant habit*.—Slightly upright and bushy.

Height and spread.—Mid size plant stature; reaching about 1.5 m in height and 1.7 m in width as a mature (25 year-old) plant.

*Cold hardiness*.—At least in U.S.D.A. Zone 4.

*Diseases and pests*.—No particular resistance or susceptibility to diseases or pests has been observed.

*Propagation*.—Semi-hardwood cuttings.

*Growth rate and vigor*.—Moderate.

*Chill requirement*.—Has not been established.

Stem description:

*Mature canes*.—197C and N200C in color, an range of 70 to 150 cm in length and 0.9 to 1.7 cm in width on a 25 year old, mature specimen plant, bark surface ranges from smooth to rough.

*Dormant stems* (*previous years growth*).—A blend of 45C and 46C in color, range from 7 to 45 cm in length and 3 mm in width, surface is glabrous to sparsely pubescent, internode length; an average of 2.2 cm, ranging from 1.6 to 2.8 cm.

*New growth*.—144B in color.

*Branching*.—Medium.

*Suckering*.—Medium.

Foliage description:

*Leaf shape*.—Elliptic.

*Leaf division*.—Simple.

*Leaf base*.—Cuneate to round-cuneate.

*Leaf apex*.—Acute.

*Leaf venation*.—Pinnate, color on upper and lower surface; midrib NN155B and occasionally suffused midway from petiole with 60A and 59B, other veins 191C.

*Leaf margins*.—Entire.

*Leaf attachment*.—Petiolate.

*Leaf arrangement*.—Alternate.

*Leaf orientation*.—Held slightly upward and cupped slightly inward.

*Leaf surface*.—Upper and lower surface glabrous and dull with occasional sparse pubescence on the leaf margin and mid vein on upper surface.

*Leaf color*.—Newly expanded leaves upper and lower surface; N144A with occasional overlay of anthocyanin coloration of N170A to give a bronzing appearance, mature leaves upper surface; 146A, mature leaves lower surface; 147B to 147C, fall color upper surface; 183A changing to N34A and finally to 45A as chlorophyll is lost, fall color lower surface; 35C when chlorophyll is lost.

*Leaf size*.—Average of 6.4 cm in length, ranging from 5.8 to 7.7 cm in length; average of 3.6 cm in width, ranging from 3 to 4.4 cm in width.

*Leaf blade length/width ratio*.—Average of 1.8, ranges from 1.6 to 2.

*Synchrony of leafing and flowering*.—Shoots have about 5 to 7 leaves at flowering.

*Petioles*.—Round in shape, an average of 4 mm in length and 1 mm in width, 60A and 59B in color, glabrous surface.

*Stipules*.—None observed.

Inflorescence description:

*Bloom season*.—Buds burst medium-early, about April 15 to 30 in Becker, Minn., flowering begins medium-early, about May 5 to 15 in Becker, Minn., bud burst and bloom time are highly variable depending on season, flowering time is after 'St. Cloud', similar to 'Northblue', 'Chippewa', and 'Polaris' and earlier than 'Northland', 'Superior' and 'Patriot' (all non patented).

*Inflorescence*.—Cluster, average of 2 cm in length 1.5 cm in width.

*Lastingness of inflorescence*.—Average of 8 days but highly dependent on temperatures.

*Number of flowers*.—Average of 7 per inflorescence, range of 5 to 8.

*Flower fragrance*.—None to slight.

*Flower size*.—Average of 7.4 mm in length and 6 mm in width.

*Flower buds*.—1 to 10 per inflorescence, ovate in shape, 3.2 mm in length and 5.4 mm in width.

*Corolla*.—Urceolate in shape, comprised of 5 fused petals with tip free and curled under, average of 5.4 mm in length and 6 mm in width, aperture is an average of 3.5 mm in diameter, color 155A on outer and inner surface with outer surface sometimes tinged with 182D with sun exposure, glabrous texture on both surfaces.

*Calyx*.—Campanulate, comprised of 5 fused sepals with lobes free at apex, average of about 2 mm in length and 62 mm in width at anthesis, color N144B on outer and inner surface and tinged at the distil end with 181B with sun exposure, surface glabrous.

*Pedicels*.—Round, average of 4.4 mm in length and 5.6 mm in length, 145A in color, surface is glabrous.

*Peduncles*.—Round, an average of 1.1 cm in length and 12.3 in width, 145A in color, surface is glabrous.

Reproductive organs:

*Androecium*.—10 stamens, stamens are 4-5 mm in length, anthers are 163B in color and 4 to 5 mm in length, filaments are 1 to 2 mm in length and 145D in color, pollen is moderate in abundance and 155A in color.

*Gynoecium.*—1 pistil, style is cone-shaped, an average of 6 mm in length (approximately equal to tip of corolla) and 137A in color, ovary N144B in color.

Fruit description:

*Type*.—Berry.

*Number.*—1 to 5 per cluster.

*Cluster tightness*.—Medium.

*Skin color*.—Unripe; 144C to 144D changing to 145C, ripening; 157C to 157D with a blush of 186D on lighter fruit and 186A and 186B on darker fruit.

*Date of fruit ripening*.—Medium-early for 50% ripe.

*Skin surface*.—Medium level of glaucous coating (bloom).

*Shape*.—Larger berries broadly elliptic, smaller berries globose-elliptic.

*Flesh color*.—A blend of 156D and N155D.

*Flesh texture*.—Fleshy.

*Calyx*.—Campanulate, comprised of 5 fused sepals with lobes free at apex, 1.5 cm in length and 6.2 mm in width, color 155A on outer and inner surface with outer surface tips tinged with 182D with sun exposure, glaucous surface, free lobes; average of 1 mm in length and 3 mm in width, triangular in shape, diameter of aperture; average of 6 mm.

*Scar size*.—Average of 3 mm in diameter.

*Flavor*.—Balance sweet-tart taste with moderate aroma.

*Firmness*.—Moderately crisp.

*Weight.*—1.55 g mean (100 berries sampled).

*Brix.*—15.1 degrees.

*Acidity.*—9.8 g/liter citric acid equivalent and pH=3.6.

*Productivity*.—Moderate.

*Storage life*.—Up to 3 weeks in refrigeration (~3° C.).

*Seeds*.—Average of 15 per berry, 165A in color, average of 1.8 mm in length and 0.65 mm in width.

*Self incompatibility*.—Less than 10% set fruit with hand pollination.

It is claimed:

1. A new and distinct cultivar of Blueberry plant named 'MNPink1' as herein illustrated and described.

* * * * *